United States Patent [19]

Malamas et al.

[11] Patent Number: 5,459,154

[45] Date of Patent: Oct. 17, 1995

[54] N-HYDROXYUREAS AS 5-LIPOXYGENASE INHIBITORS AND INHIBITORS OF OXIDATIVE MODIFICATION OF LOW DENSITY LIPOPROTEIN

[75] Inventors: Michael S. Malamas, Jamison; James A. Nelson, Washingtons Crossing, both of Pa.

[73] Assignee: American Home Products Corporation, Madison, N.J.

[21] Appl. No.: 148,603

[22] Filed: Nov. 8, 1993

[51] Int. Cl.⁶ ............ C07D 263/32; C07D 277/30; A61K 31/425; A61K 31/42
[52] U.S. Cl. .............. 514/374; 514/365; 548/204; 548/236
[58] Field of Search ............... 548/204, 236; 514/365, 374

[56] References Cited

FOREIGN PATENT DOCUMENTS

| | | | |
|---|---|---|---|
| 0279281 | 2/1988 | European Pat. Off. | C07C 127/19 |
| 0384594 | 8/1988 | European Pat. Off. | C07C 275/64 |
| WO90/12008 | 10/1990 | WIPO | C07D 331/00 |
| WO92/03425 | 3/1992 | WIPO | C07D 263/32 |
| WO92/03130 | 3/1992 | WIPO | A61K 31/34 |

OTHER PUBLICATIONS

Reaven et al., Arteriosclerosis and Thrombosis 12(3), 318–21 (1992).
Steinberg, Amer J. of Cardiology 57, 16H–21H, (1986).
Carew, Schwenke and Steinberg, Proc. Natl. Acad. Sci. 84, 7725–29 (1987).
Nagano et al., Arteriosclerosis 9(4), 453–461 (1989).

Primary Examiner—Robert Gerstl
Attorney, Agent, or Firm—R. F. Boswell, Jr.

[57] ABSTRACT

This invention relates to compounds having 5-lipoxygenase inhibiting properties and inhibition of oxidative modification of low density lipoprotein which have the formula:

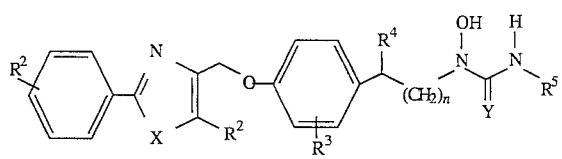

wherein:

$R^1$ and $R^3$ are independently hydrogen, halogen, $C_1$-$C_6$ alkyl, $C_1$-$C_6$ alkoxy, trifluoromethyl, or $C_1$-$C_6$ trifluoroalkoxy;

$R_2$ is hydrogen or methyl;

$R^4$ is hydrogen, methyl or hydroxy;

$R^5$ is hydrogen, —$NH_2$, $C_1$-$C_6$ alkyl, aryl, aralkyl, or —$N$=$C(CH_3)_2$;

X and Y are independently O or S;

and n is 0 or 1; or a pharmaceutically acceptable salt thereof. Compounds which inhibit 5-lipoxygenase are useful in the treatment of diseases mediated by leukotrienes such as inflammation or bronchoconstriction. Compounds which inhibit oxidative metabolism of low density lipoprotein are useful in the inhibition of atherosclerotic plaque formation.

6 Claims, No Drawings

N-HYDROXYUREAS AS 5-LIPOXYGENASE INHIBITORS AND INHIBITORS OF OXIDATIVE MODIFICATION OF LOW DENSITY LIPOPROTEIN

The N-hydroxy ureas of this invention inhibit 5-lipoxygenase, thus inhibiting the synthesis of leukotrienes which are mediators in the inflammatory response and bronchoconstriction and inhibit the oxidative modification of low density lipoprotein associated with formation of atherosclerotic plaque.

BACKGROUND OF THE INVENTION

Leukotrienes participate in inflammatory reactions, exhibit chemotactic activities, stimulate lysosomal enzyme release and act as important factors in the intermediate hypersensitivity reaction. Leukotrienes are metabolic products of metabolism of arachidonic acid (AA) by lipoxygenase enzymes with the most significant leukotrienes being $LTB_4$, $LTC_4$, $LTD_4$ and $LTE_4$. The latter three leukotrienes are incorporated in the substance known as SRS or SRS-A, the slow-reacting substance of anaphylaxis [J. Immun. 215, 115–118 (1980), Biochem. Biophys. Res. Comm. 93, 1121–1126(1980)]. By another metabolic pathway, arachidonic acid is metabolized by cyclooxygenase enzymes to prostaglandins and thromboxanes.

Leukotrienes $LTC_4$ and $LTD_4$ are potent bronchoconstrictors of the human bronchi [Dahlen et al., Nature 288, 484–486 (1980) and Piper, Int. Arch, Appl. Immunology 76, Suppl. 1, 43 (1985)] which stimulate the release of mucus from airways in vitro [Macom et al., Am. Rev. Resp. Dis. 126, 449 (1982)], are potent vasodilators in skin [Bisgaard et al., Prostaglandins 23, 797 (1982)], and produce a wheal and flare response [Camp et al., Brit. J. Pharmacol. 80 497 (1983)]. The nonpeptide leukotriene $LTB_4$ is a powerful chemotactic factor for leukocytes [A. S. Ford-Hutchinson, J. Royal Soc. Med. 74, 831–883 (1981)], which stimulates cell accumulation and affects vascular smooth muscle [Bray, Brit. Med. Bull. 39, 249 (1983)]. The activity of leukotrienes as mediators of inflammation and hypersensitivity is extensively reviewed [Bailey and Casey, Ann. Reports Med. Chem. 17, 203–217 (1982) and Bray, Agents and Actions 19, 87 (1986) and Masamune and Melvin, Ann. Reports Med. Chem. 24, 71 (1989)].

There is also evidence that products of the cyclooxygenase/lipoxygenase pathways play key roles in both the pathogenesis of gastric mucosal damage due to extracellular (gastric and intestinal contents, microorganisms, and the like) or intracellular (ischemia, viruses, etc.) agents, as well as in cytoprotection against such damage. Thus, on the one hand prostaglandins exert a cytoprotective effect on the gastric mucosa [see Robert, Gastroenterology, 77, 761–767 (1979)] and this action of the prostaglandins, especially of the E series, is considered to be of importance in the treatment of gastrointestinal ulceration [see Isselbacher, Drugs, 33 (suppl.), 38–46 (1987)]. On the other hand, ex vivo experiments have shown that gastric mucosal tissue from ethanol-pretreated rats is capable of $LTC_4$ generation and that this $LTC_4$ production is quantitatively related to the severity of the ethanol damage [see Lange et al., Naunyn-Schmiedeberg's Arch. Pharmacol. Suppl., 330, R27, (1985)]. It has also been demonstrated that $LTC_4$ can induce vasoconstriction in both venous and aneriolar vessels in the rat submucosa [see Whittle, IUPHAR Ninth Int. Cong. of Pharmac., S30-2, London, England (1984)]. This is significant since ethanol-induced lesion formation in gastric mucosa may be multifactorial with, for example, stasis of gastric blood flow contributing significantly to the development of the hemorrhagic necrotic aspects of the tissue injury [see Guth et al., Gastroenterology, 87, 1083–90 (1984)]. Moreover, in the anesthetized cat, exogenous $LTD_4$ evokes both increased pepsin secretion and decreased transgastric potential [Pendleton et al., Eur. J. Pharmacol., 125, 297–99 (1986)]. A particularly significant recent finding in this regard is that 5-lipoxygenase inhibitors and some leukotdene antagonists protect the gastric mucosa against lesions induced by the oral or parenteral administration of most nonsteroidal antiinflammatory drugs [see Rainsford, Agents and Actions, 21, 316–19 (1987)]. Accordingly, a significant body of evidence implicates the involvement of lipoxygenase products in the development of pathological features associated with gastric mucosal lesions, such as for example those induced by ethanol exposure and administration of non-steroidal anti-inflammatory drugs. Thus, compounds which inhibit the biological effects of leukotrienes and/or which control the biosynthesis of these substances, as by inhibiting 5-lipoxygenase, are considered to be of value as cytoprotective agents.

Accordingly, the biological activity of the leukotrienes and SRS's, and of lipoxygenase as the enzyme leading to the metabolism of AA to leukotrienes, indicates that a rational approach to drug therapy to prevent, remove or ameliorate the symptoms of allergies, anaphylaxis, asthma and inflammation and for gastric cytoprotection must focus on either blocking the release of mediators of these conditions or antagonizing their effects. Thus compounds, which inhibit the biological effects of the leukotrienes and SRS's and/or which control the biosynthesis of these substances, as by inhibiting lipoxygenase, are considered to be of value in treating such conditions as allergic bronchial asthma, allergic rhinitis, as well as in other immediate hypersensitivity reactions and in providing gastric cytoprotection.

Compounds of this invention inhibit lipoxygenase and antagonize products of the lipoxygenase pathway and thus are useful as antiinflammatory and anti-allergic agents. Compounds of this invention are expected to have gastric cytoprotective activity.

Atherosclerosis, the underlying disease kmplicated in myocardial infarction and strokes, is a complex pathologic process involving the intimal layer of the arteries. The earliest lesion of atherosclerosis is development of the fatty streak lesions which contain lipid-laden macrophages and lipid-laden smooth muscle cells. Macrophages do not take up native low density lipoprotein (LDL) but do take up modified, i.e., acetylated LDL or oxidized LDL via acetyl-LDL or "scavenger" receptors to form the foam cells of atherosclerotic plaque. Free radial oxidation, i.e., lipid peroxidation, has been shown to be involved in the alteration of LDL by endothelial cells. Arterial smooth muscle cells generate superoxide and oxidize LDL in the presence of micromolar concentrations of $Cu^{+2}$ or $Fe^{+2}$. The way LDL can be modified by endothelial cells can be mimicked in vitro by incubation of the lipoprotein in the presence of $CuCl_2$. Probucol, an antihyperlipidemic agent, also inhibits both cell mediated and $Cu^{+2}$ mediated oxidative modification of LDL, and was shown to inhibit the formation of atherosclerotic lesions in WHHL rabbits [Reaven et al., Arteriosclerosis and Thrombosis 12(3), 318–324 (1992), Steinberg, The Amer. J. of Cardiology 57, 16H–21H (1986), Carew. Schwenke and Steinberg, Proc. Natl. Acad. Sci. 84, 7725–7729 (1987) and Nagano et al., Arteriosclerosis 9 (4), 453–461 (1989)]. Thus in vitro inhibition of $Cu^{+2}$ catalyzed oxidation of LDL is indicative of antiatherosclerotic utility.

Compounds of this invention inhibit in vitro the copper-induced peroxidation of LDL and thus would be useful in the treatment or prevention of arteriosclerosis.

Lipoxygenase inhibiting compounds of the formula:

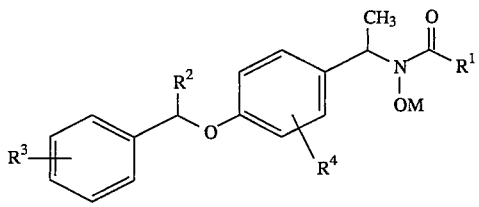

wherein $R^1$ is amino or methyl, $R^2$ is $C_1$-$C_2$ alkyl, $R^3$ is selected from hydrogen, halogen, and trihalomethyl; $R^4$ is hydrogen, halogen, trihalomethyl, $C_1$-$C_4$ alkoxy or $C_1$-$C_4$ alkyl; and M is hydrogen, a pharmaceutically acceptable cation, aroyl or $C_1$-$C_6$ alkoyl are disclosed in EP 0279281 A2. EP 0384594 A1 discloses antiinflammatory 5-lipoxygenase inhibitors of the formula:

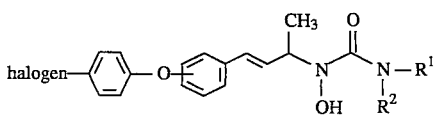

wherein $R^1$ and $R^2$ are selected from H and $C_1$-$C_4$ alkyl independently and the 4-halophenoxy moiety can be attached to the phenyl ring at either the 3 or 4 position.

The PCT patent WO 90/12008 discloses lipoxygenase inhibiting compounds of the formula:

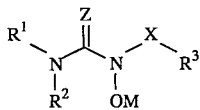

wherein M is, among other choices, hydrogen or a pharmaceutically acceptable cation; Z is O or S; X is a straight or branched $C_1$-$C_6$ alkylene or $C_2$-$C_6$ alkenylene group optionally substituted by hydroxy, halogen, cyano, alkoxy, aminocarbonyl, carboxy and alkoxycarbonyl; $R^1$ and $R^2$ are independently hydrogen, hydroxy, or $C_1$-$C_6$ alkyl optionally substituted by hydroxy, halogen, cyano, alkoxy, etc., with a proviso that both $R^1$ and $R_2$ cannot hydroxy; and $R_3$ can be phenyl, naphthyl or thienyl optionally substituted by a variety of substituents including carbocyclic or heterocyclic arylalkoxy groups optionally substituted by halogen, nitro, cyano, alkyl, alkoxy or halosubstituted alkyl wherein the heterocyclic aryl moiety is defined as a 5 to 6 membered ring containing one N, S, or O atom or a N and O or a N and S or three N atoms and further stipulates that the 5 to 6 membered heterocyclicaryl moiety may be fused with a phenyl ring to form a benzo-fused heterocycle. The PCT application WO 92/03425 discloses compounds that are intermediates to antidiabetic compounds having the formula:

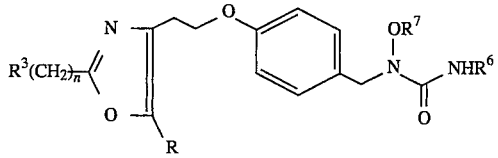

wherein n is 0 or 1, R is hydrogen or $C_1$-$C_3$ alkyl, $R^3$ is one of $C_1$-$C_9$ alkyl, $C_3$-$C_7$ cycloalkyl, phenyl, naphthyl, furyl, benzofuryl or thienyl optionally substituted with one or two groups selected from $C_1$-$C_3$ alkyl, $C_1$-$C_3$ alkoxy, $C_1$-$C_3$ alkoxycarbonyl, trifluoromethyl, fluoro or chloro; $R^6$ is hydrogen, $C_1$-$C_9$ alkyl, $C_3$-$C_7$ cycloalkyl, phenyl, naphthyl, furyl, benzofuryl or thienyl and $R^7$ is hydrogen or a conventional protecting group. N-Aryl-N-hydroxy ureas, formamides and alkylamides having previously been disclosed to have lipoxygenase inhibiting activity, are disclosed in WO 92/03130 as having anti-atherosclerotic activity and have the formula:

Ar—Y—Q wherein Ar is heteroaromatic, naphthyl, tetrahydronaphthyl, phenyl or phenyl substituted by phenyl, naphthyl or a heteroaromatic group; Y is $C_1$-$C_{10}$ alkylene or $C_2$-$C_{10}$ alkylene and Q is

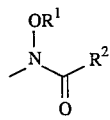

where $R^1$ is H, $C_1$-$C_4$ alkyl or an Ar group and $R^2$ is H, $C_1$-$C_4$ alkyl, amino, mono or dialkylamino, cycloalkylamino, cycloalkylalkylamino, anilino, N-alkylanilino or an Ar group.

SUMMARY OF THE INVENTION

The compounds useful in the methods and pharmaceutical compositions of this invention are represented by Formula I:

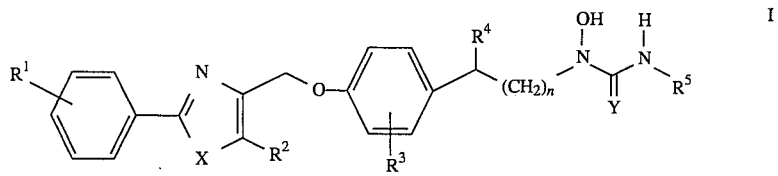

wherein:

$R^1$ and $R^3$ are independently hydrogen, halogen, $C_1$-$C_6$ alkyl, $C_1$-$C_6$ alkoxy, trifluoromethyl, or $C_1$-$C_6$ trifluoroalkoxy;

$R^2$ is hydrogen or methyl;

$R^4$ is hydrogen, methyl or hydroxy;

$R^5$ is hydrogen, —$NH_2$, $C_1$-$C_6$ alkyl, aryl, aralkyl, or —N=C(CH$_3$)$_2$;

X and Y are independently O or S;

and n is 0 or 1; or a pharmaceutically acceptable salt thereof. The terms halogen, $C_1$-$C_6$ alkyl, $C_1$-$C_6$ alkoxy, $C_1$-$C_6$ trifluoroalkoxy, aryl and aralkyl are further defined. hereinbelow. The term halogen means fluorine, chlorine, bromine, or iodine. The term $C_1$-$C_6$ alkyl includes both straight and branched chain hydrocarbon groups such as methyl, ethyl, propyl, isopropyl, n-butyl, sec-butyl, t-butyl and the like. The term $C_1$-$C_6$ alkoxy denotes a -O-$C_1$-$C_6$ alkyl group where $C_1$-$C_6$ alkyl is as defined above. The term $C_1$-$C_6$ trifluoroalkoxy means a -O-$C_1$-$C_6$ alkyl group where three hydrogens of a methyl group are replaced by fluorines, preferably trifluoromethoxy or 2,2,2-trifluoroethoxy. The term aryl refers to a phenyl or naphthyl group and the term aralkyl refers to a $C_6$-$C_{10}$ aryl group attached to a $C_6$-$C_{10}$ alkylene group, such as benzyl, phenylethyl, or naphthylmethyl. The term pharmaceutically acceptable salt refers to a solvate, hydrate, or acid addition salt which can be formed from an invention compound and a pharmaceutically acceptable inorganic or organic acid including but not limited to such acids as hydrochloric, hydrobromic, sulfufic, phosphoric, acetic, maleic, fumaric, citric, succinic, hexamic, tartaric, and methanesulfonic acids.

The compounds of this invention are shown to inhibit 5-lipoxygenase in in vitro and ex vivo assays as evidenced by inhibition of leukotriene $B_4$ (LTB$_4$) and thus would be useful in the treatment of diseases mediated by leukotrienes such as inflammation and bronchoconstriction. The invention compounds also inhibit the oxidative modification of low density lipoprotein to the diene form and thus are useful in inhibiting formation of atherosclerotic plaque.

Objects of this invention are to provide novel compounds useful for the treatment of inflammation, bronchoconstriction and inhibiting the formation of atherosclerotic plaque, and pharmaceutical compositions.

DETAILED DESCRIPTION OF THE INVENTION

The compounds of this invention can be prepared according to the following reaction schemes. In the reaction schemes, the variables $R^1$-$R^5$, Z, X, and n are as defined above.

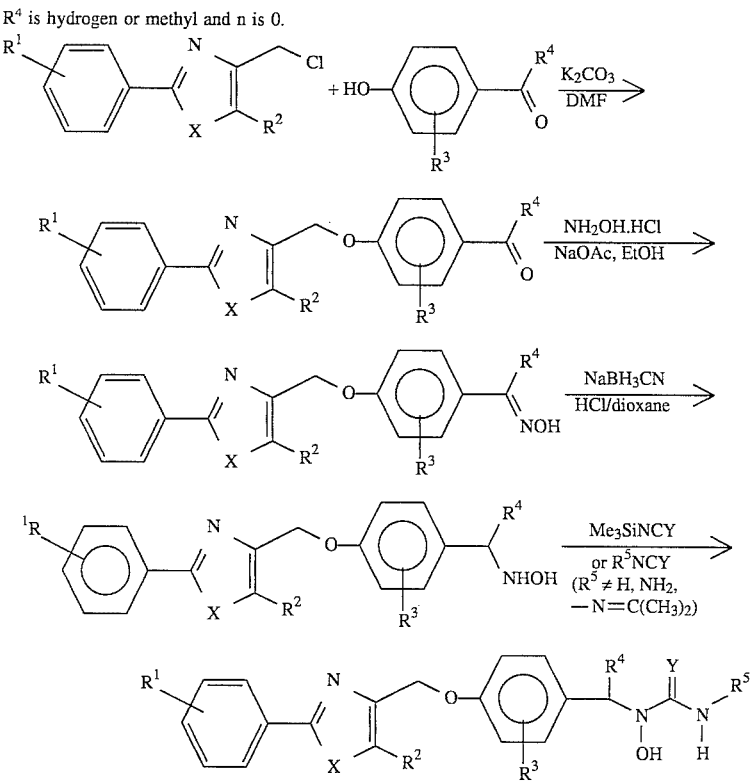

5,459,154
Scheme II.
$R^4$ is hydroxy and n is 1.
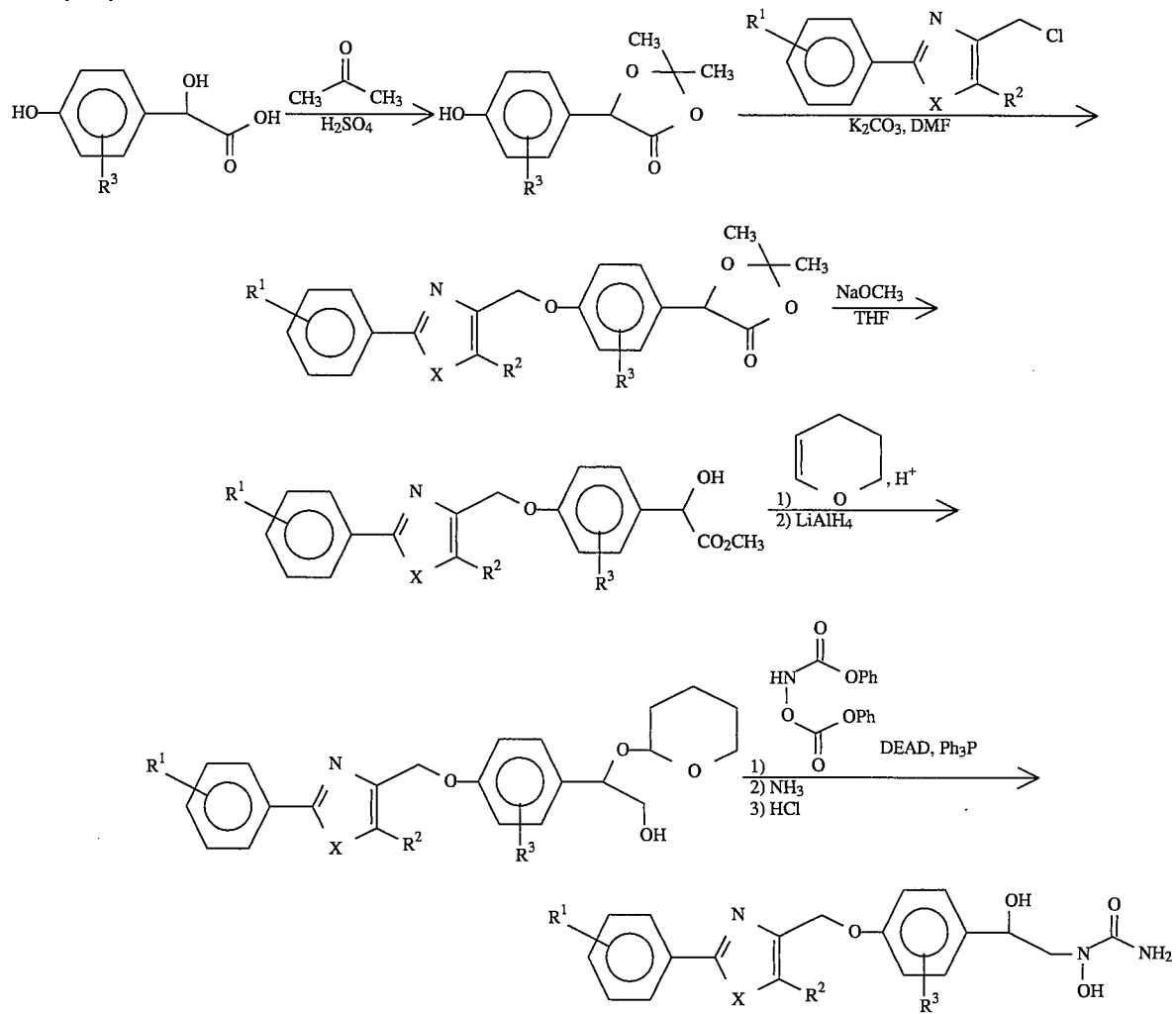
Scheme III.
$R^5$ is amino or $-N=C(CH_3)_2$.
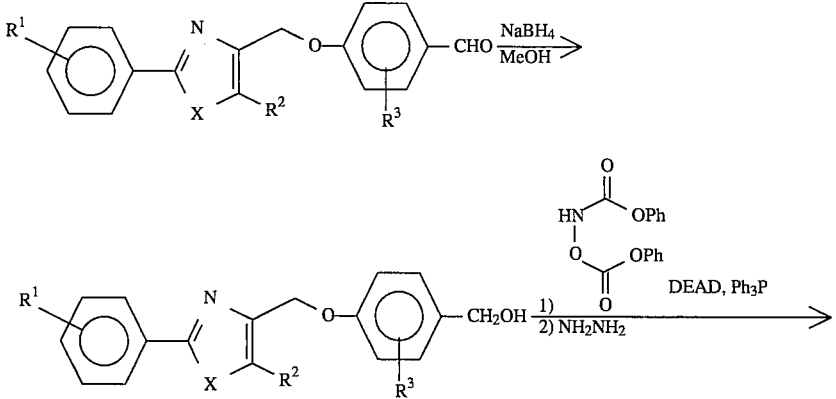

Scheme III.
-continued

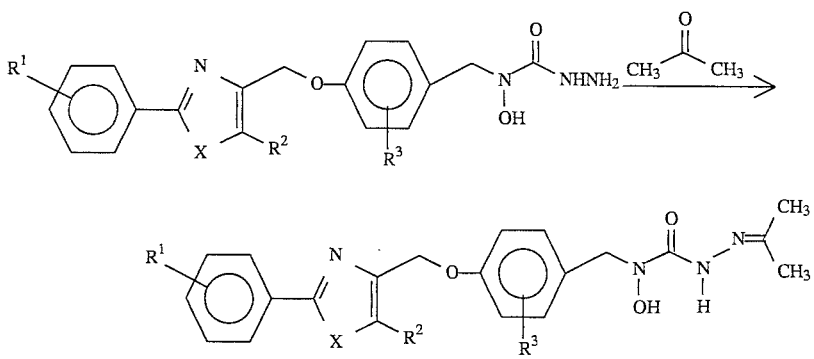

The intermediate 2-phenyl-4-chloromethyl-5-(H or methyl) oxazoles and thiazoles can be prepared by known methods conventional in the art (*Heterocyclic Compounds* 34, 1979 and *Heterocyclic Compounds* 45, 1986). The 2-phenyl-4-chloromethyl-5-methyloxazoles can be prepared according to the reaction sequence shown in Scheme IV.

Scheme IV

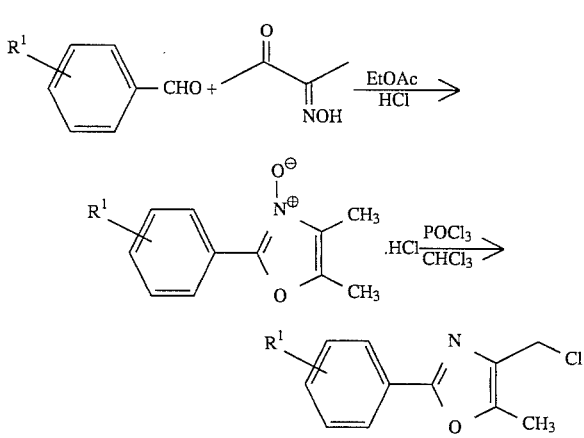

The intermediate 4-chloromethyl-2-phenyloxazoles or thiazoles can be prepared according to the reaction shown in Scheme V.

Scheme VI

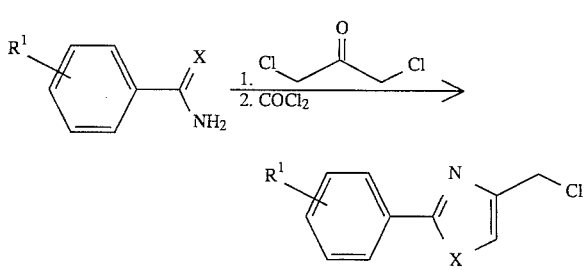

X = O or S

The following specific examples are included for illustrative purposes only and are not to be construed as limiting to the scope of the invention. Other synthetic procedures may be apparent to those skilled in the art. In the following examples, reagents and intermediates are either commercially available or can be prepared according to standard literature procedures by those skilled in the art.

EXAMPLE 1

1-Hydroxy-1-[4-(5-methyl-2-phenyl-oxazol-4-yl-methoxy)-benzyl]-urea

Step a) 4-(5-methyl-2-phenyl-oxazol-4-ylmethoxy)-benzaldehyde

A mixture of 4-chloromethyl-5-methyl-2-phenyl-oxazole (5.5 g, 26.5 mmol), 4-hydroxybenzaldehyde (3.23 g, 26.5 mmol), potassium carbonate (3.66 g, 26.5 mL) and N,N-dimethylformamide (80 mL) was stirred at 80° C. for 8 hours. The mixture was poured into $H_2O$ and extracted with EtOAc. The organic extracts were dried over $MgSO_4$. Evaporation and purification by flash chromatography on silica gel (eluting solvent hexane/EtOAc 4/1) gave a yellow solid (6.8 g, 86% yield, m.p. 103°–105° C.).

Analysis for: $C_{18}H_{15}NO_3$ Calc'd: C, 73.71; H, 5.15; N, 4.78 Found: C, 73.77; H, 5.13; N, 4.66

Step b) 4-(5-methyl-2-phenyl-oxazol-4-ylmethoxy)-benzaldehyde oxime

In to a solution of 4-(5-methyl-2-phenyl-oxazol-4-yl-methoxy)-benzaldehyde (6.5 g, 22.2 mmol) in ethanol (300 mL) were added hydroxylamine hydrochloride (4.62 g, 66.55 mmol) and a solution of sodium acetate (7.27 g, 82.7 mmol) in $H_2O$ (40 mL). The mixture was stirred at room temperature for 12 h, then poured into $H_2O$, acidified with 1N HCl and extracted with EtOAc. The organic extracts were dried over $MgSO_4$. Evaporation and crystallization from acetone/ether/hexane, gave a white solid (6.1 g, 89% yield, m.p. 192°–193° C.).

Analysis for: $C_{18}H_{16}N_2O_3$ Calc'd: C, 70.12; H, 5.23; N, 9.09 Found: C, 70.31; H, 5.27; N, 8.82

Step c) N-[4-(5-methyl-2-phenyl-oxazol-4-ylmethoxy)-benzyl]-hydroxylamine

In to a solution of 4-(5-methoxy-2-phenyl-oxazol-4-yl-methoxy)-benzaldehyde oxime (6.0 g, 19.42 mmol) in MeOH (300 mL) and THF (60 mL) were added sodium cyanoborohydride (6.05 g, 97.1 mmol) and methyl orange (indicator, 20 mg). A solution of 4N HCl in dioxane was added dropwise in a rate that maintained the pH solution at a range 3–4. When a persistent red color was observed, the reaction mixture was poured into $H_2O$, basified with 1N NaOH to pH 9 and extracted with EtOAc. The organic extracts were dried over MgSO$_4$. Evaporation and purification by flash chromatography, on silica gel (eluting solvent EtOAc/MeOH 10/1) gave a yellow solid (5.2 g, 86% yield, m.p. 109°–110° C).

Analysis for: C$_{18}$H$_{18}$N$_2$O$_3$ Calc'd: C, 69.66; H, 5.85; N, 9.03 Found: C, 69.79; H, 5.83; N, 8.92

Step d) 1-Hydroxy-1-[4-(5-methyl-2-phenyl-oxazol-4-ylmethoxy)benzyl]urea

In to a solution of N-[3-(5-methyl-2-phenyl-oxazol-4-ylmethoxy)-benzyl]-hydroxylamine (1.25 g, 4.03 mmol) in dioxane (20 mL) was added trimethylsilylisocyanate (0.85 mL, 6.05 mmol). The mixture was stirred at room temperature for 2 hours, poured into H$_2$O, acidified with 2N HCl and extracted with EtOAc. The organic extracts were dried over MgSO$_4$. Evaporation and crystallization from acetone/ether, gave a white solid (1.05 g, 74% yield, m.p. 157°–159° C.).

Analysis for: C$_{19}$H$_{19}$N$_3$O$_4$ Calc'd: C, 64.58; H, 5.42; N, 11.89 Found: C, 64.73; H, 5.49; N, 11.86

EXAMPLE 2

1-[3-Chloro-4-(5-methyl-2-phenyl-oxazol-4-ylmethoxy)-benzyl]-1-hydroxy urea

The title compound was prepared in substantially the same manner as described in example 1, steps a–d, and was obtained as a white solid, m.p. 180°–182° C.

Analysis for: C$_{19}$H$_{18}$ClN$_3$O$_4$ Calc'd: C, 58.84; H, 4.68; N, 10.84 Found: C, 59.09; H, 4.57; N, 10.52

EXAMPLE 3

1-[2-Chloro-4-(5-methyl-2-phenyl-oxazol-4-ylmethoxy)-benzyl]-1-hydroxy urea

The title compound was prepared in substantially the same manner as described in example 1, steps a–d, and was obtained as a light brown solid, m.p. 145°–147° C.

Analysis for: C$_{19}$H$_{18}$ClN$_3$O$_4$ Calc'd: C, 58.84; H, 4.68; N, 10.84 Found: C, 59.09; H, 4.57; N, 10.53

EXAMPLE 4

1-Hydroxy-1-[3-methoxy-4-(5-methyl-2-phenyl-oxazol-4-ylmethoxy)-benzy]urea

The title compound was prepared in substantially the same manner as described in example 1, steps a–d, and was obtained as a light yellow solid, m.p. 138°–139° C.

Analysis for: C$_{20}$H$_{21}$N$_3$O$_5$ Calc'd: C, 62.65; H, 5.52; N, 10.96 Found: C, 62.92; H, 5.59; N, 10.63

EXAMPLE 5

1-[3-Fluoro-4-(5-methyl-2-phenyl-oxazol-4-ylmethoxy)-benzyl]-1-hydroxy urea

The title compound was prepared in substantially the same manner as described in example 1, steps a–d, and was obtained as a white solid, m.p. 143°–144° C.

Analysis for: C$_{19}$H$_{18}$FN$_3$O$_4$ Calc'd: C, 61.45; H, 4.88; N, 11.31 Found: C, 61.47; H, 4.79; N, 11.43

EXAMPLE 6

1-Hydroxy-1-[4-[5-methyl-2-(4-trifluoromethyl-phenyl)-oxazol-4-ylmethoxy]-benzyl]-urea The title compound was prepared in substantially the same manner as described in example 1, steps a–d, and was obtained as a white solid, m.p. 146°–147° C.

Analysis for: C$_{20}$H$_{18}$F$_3$N$_3$O$_4$ Calc'd: C, 57.01; H, 4.31; N, 9.97 Found: C, 56.99; H, 4.33; N, 9.87

EXAMPLE 7

1-Hydroxy-1-[4-[5-methyl-2-(4-trifluoroethoxy-phenyl)-oxazol-4-ylmethoxy]-benzyl]-urea The title compound was prepared in substantially the same manner as described in example 1, steps a–d, and was obtained as a white solid, m.p. 159°–161° C.

Analysis for: C$_{21}$H$_{20}$F$_3$N$_3$O$_5$ Calc'd: C, 55.88; H, 4.47; N, 9.31 Found: C, 56.24; H, 4.55; N, 9.07

EXAMPLE 8

1-Hydroxy-1-[1-[-4-[5-methyl-2-phenyl-oxazol-4-ylmethoxy)-phenyl]-ethyl]-urea

The title compound was prepared in substantially the same manner as described in example 1, steps a–d. 3'-Hydroxyacetophenone is used in place of 3-hydroxybenzaldehyde The title compound was obtained as a white solid, m.p. 123°–124° C.

Analysis for: C$_{20}$H$_{21}$N$_3$O$_4$ Calc'd: C, 65.38; H, 5.76; N, 11.44 Found: C, 65.20; H, 5.79; N, 11.33

EXAMPLE 9

1-Hydroxy-1-[4-(2-phenyl-oxazol-4-ylmethoxy)-benzyl]-urea step a) 4-(2-phenyl-oxazol-4-ylmethoxy)benzaldehyde A mixture of 4-hydroxybenzaldehyde (1.9 g, 17.0 mmol), dimethyl sulfoxide (50 mL), 2-(chloromethyl)- 2-phenyloxazole (3.3 g, 17.0 mmol) and cesium carbonate (11.0 g, 34.0 mmol) was stirred at room temperature for 16 hours. The mixture was poured into water (400 mL) and filtration of the resultant precipitate afforded the crude product. Crystallization of the solids from ethyl acetate gave the product as a light yellow solid in 90.5% yield, m.p. 94°–96° C. MS (EI, m/e): 279 (M)$^+$ step b) 4-(2-phenyl-oxazol-4-ylmethoxy)benzaldehyde oxime A solution of 4-(2-phenyl-oxazol-4-ylmethoxy)benzaldehyde (4.3 g, 15.3 mmol), ethanol (100 mL), pyridine (45 mL) and hydroxylamine hydrochloride (2.2 g, 30.8 mmol) was refluxed for 1.5 hours. The solution is cooled to 25° C. and poured into water (600 mL). The resultant precipitate was filtered and dried at 25° C. for 18 hours to give the product as a white solid in 97.1% yield, m.p. 184°–186° C. MS (EI, m/e): 294 (M)$^+$.

step c) N-hydroxy-N-[4-(2-phenyl-oxazol-4-ylmethoxy)-phenyl-1-ylmethyl]-amine

To a stirred solution containing 4-(2-phenyl-oxazol-4-ylmethoxy)-benzaldehyde oxime (2.0 g, 6.8 mMol) in acetic acid (100 mL) at 25° C., was added, in small portions over 30 minutes, solid sodium cyanoborohydride (2.0 g, 31.8 mmol). The mixture is stirred for 4 hours, concentrated under reduced pressure and dilluted with water (300 mL). The resulting precipitate was filtered and the solids were dissolved in ethyl acetate (500 mL). The organic solution was washed with water (2×200 mL), and with brine (200 mL), dried over MgSO$_4$ and concentrated to a colorless oil. This oil was crystallized from hexane to give the product as a white solid in 69.5% yield, m.p. 105°–108° C. (decomposed). MS (EI, m/e): 296 (M)$^+$.

step d) 1-Hydroxy-1-[4-(2-phenyl-oxazol-4-ylmethoxy)-benzyl]-urea

A mixture containing N-hydroxy-N-[4-(2-phenyl-oxazol- 4-ylmethoxy)-phenyl-1-ylmethyl]-amine (1.2 g, 4.05 mmol), dioxane (50 mL) and trimethylsilylisocyanate (2.2 mL, 16.2 mmol) was stirred for 3 hours. The mixture was poured into saturated ammonium chloride (mL) and after stirring for 30 minutes, the solids were filtered to give the crude product. Crystallization from hexane gave the title compound as a white solid in 68.6% yield, m.p. 162°–163° C. (decomposed).

Analysis for: $C_{18}H_{17}N_3O_4$ Calc'd: C, 63.71; H, 5.05; N, 12.38. Found: C, 63.67; H, 5.10; N, 12.21.

EXAMPLE 10

1-Hydroxy-1-[4-(2-phenyl-thiazol-4-ylmethoxy)-benzyl]-urea step a) 4-(2-phenyl-thiazol-4-ylmethoxy)benzaldehyde The title compound was prepared similar to the method described in example 1, step a, and was obtained as a white solid, m.p. 86°–90° C.

Analysis for: $C_{17}H_{13}NO_2S$ Calc'd: C, 69.13; H, 4.44; N, 4.74. Found: C, 69.06; H, 4.51; N, 4.62.

step b) 4-(2-phenyl-thiazol-4-ylmethoxy)benzaldehyde oxime

The title compound was prepared similar to the method described in example 1, step b, and was obtained as a white solid, m.p. 175°–179°

Analysis for: $C_{17}H_{14}N_2O_2S$ Calc'd: C, 65.79; H, 4.55; N, 9.03. Found: C, 65.71; H, 4.60; N, 8.90.

step c) N-hydroxy-N-[4-(2-phenyl-thiazol-4-ylmethoxy)-phenyl-1-ylmethyl]-amine

The title compound was prepared similar to the method described in example 1, step c, and was obtained as a colorless oil. Without further purification, this oil was used in the next step.

step d) 1-Hydroxy-1-[4-(2-phenyl-thiazol-4-ylmethoxy)-benzyl]-urea

The title compound was prepared similar to the method described in example 1, step d, and was obtained as a white solid, m.p. 161°–164° C.

Analysis for: $C_{18}H_{17}N_3O_3S$ Calc'd: C, 60.82; H, 4.82; N, 11.82. Found: C, 61.01; H, 4.86; N, 11.67.

EXAMPLE 11

1-Hydroxy-1-[4-[2-(4-trifluoromethyl-phenyl)-oxazol-4-ylmethoxy]-benzyl]-urea step a) 4-[2-(4-trifluoromethyl-phenyl)-oxazol-4-ylmethoxy]-benzaldehyde The title compound was prepared similar to the method described in example 1, step a, and was obtained as a yellowish colored solid, m.p. 128°–130° C.

Analysis for: $C_{18}H_{12}F_3NO_3$ Calc'd: C, 62.25; H, 3.48; N, 4.03. Found: C, 62.13; H, 3.21; N, 4.09.

step b 4-[2-(4-trifluoromethyl-phenyl)-oxazol-4-ylmethoxy]-benzaldehyde oxime

The title compound was prepared similar to the method described in example 1, step b, and was obtained as a white solid, m.p. 182°–187° C.

Analysis for: $C_{18}H_{13}F_3N_2O_3$ Calc'd: C, 59.67; H, 3.62; N, 7.73. Found: C, 59.82; H, 3.33; N, 7.75.

step c) N-hydroxy-N-[4-[2-(4-trifluoromethyl-phenyl)-oxazol-4-ylmethoxy]-phenyl-1-ylmethyl]-amine The title compound was prepared similar to the method described in example 1, step c, and was obtained as a white solid, m.p. 155°–160° C. MS (EI, m/e): 365 (M)⁺.

step d) 1- Hydroxy-1-[4-[2-(4-trifluoromethyl-phenyl)-oxazol-4-ylmethoxy]-benzyl]-urea The title compound was prepared similar to the method described in example 1, step d, and was obtained as a white solid in 32.3% yield, m.p. 181°–183° C.

Analysis for: $C_{19}H_{16}F_3N_3O_4$ Calc'd: C, 56.02; H, 3.96; N, 10.32. Found: C, 56.18; H, 3.57; N, 10.34.

EXAMPLE 12

1-Hydroxy-1-[4-[2-(4-trifluoromethyl-phenyl)-thiazol-4-ylmethoxy]-benzyl]-urea step a) 4-[2-(4-trifluoromethyl-phenyl)-thiazol-4-ylmethoxy]-benzaldehyde The title compound was prepared. similar to the method described in example 1, step a, and was obtained as a solid in 45.2% yield, m.p. 104°–105° C.

Analysis for: $C_{18}H_{12}F_3NO_2S$ Calc'd: C, 59.50; H, 3.33; N, 3.85. Found: C, 59.29; H, 3.22; N, 3.64.

step b) 4-[2-(4-trifluoromethyl-phenyl)-thiazol-4-ylmethoxy]-benzaldehyde oxime

The title compound was prepared similar to the method described in example 1, step b, and was obtained as a white solid in 96.1% yield, m.p. 166°–168° C.

Analysis for: $C_{18}H_{13}F_3N_2O_2S$ Calc'd: C, 57.14; H, 3.46; N, 7.40. Found: C, 56.90; H, 3.30; N, 7.48.

step c) N-hydroxy-N-[4-[2-(4-trifluoromethyl-phenyl)-thiazol-4-ylmethoxy]-phenyl-1-ylmethyl]-amine The title compound was prepared similar to the method described in example 1, step c, and was obtained as a solid in 95.2% yield, m.p. 128°–130° C.

Analysis for: $C_{18}H_{13}F_3N_2O_2S$ Calc'd: C, 56.84; H, 3.97; N, 7.36. Found: C, 56.69; H, 3.92; N, 7.38.

step d) 1-Hydroxy-1-[4-[2-(4-trifluoromethyl-phenyl)-thiazol-4-yl-methoxy] -benzyl]-urea The title compound was prepared similar to the method described in example 1, step d, and was obtained as a white solid in 65.5% yield, m.p. 169°–170° C. (decomposed).

Analysis for: $C_{19}H_{16}F_3N_3O_3S$ Calc'd: C, 53.90; H, 3.81; N, 9.92 Found: C, 53.85; H, 3.66; N, 9.85

EXAMPLE 13

3-(4-Fluoro-phenyl)-1-hydroxy-1-[4-[2-(4-trifluoromethyl-phenyl)-thiazol-4-ylmethoxy] -benzyl]-urea The title compound was prepared. similar to the method described in example 1, step d, except that 4-fluorophenyl-isocyanate was used in place of trimethylsilylisocyanate. The product was obtained as a white solid in 58.7% yield, m.p. 174°–176° C.

Analysis for: $C_{25}H_{19}F_4N_3O_3S$ Calc'd: C, 58.02; H, 3.70; N, 8.12. Found: C, 57.94; H, 3.56; N, 8.04.

EXAMPLE 14

1-[4-[2-(4-chloro-phenyl)-thiazol-4-ylmethoxy]-benzyl]-1-hydroxy-urea step a) 4-[2-(4-chloro-phenyl)-thiazol-4-ylmethoxy]-benzaldehyde The title compound was prepared similar to the method described in example 1, step a, and was obtained as a solid in 83.5% yield, m.p. 136°–138° C.

Analysis for: $C_{17}H_{12}ClNO_2S$ Calc'd: C, 61.91; H, 3.67;

N, 4.25. Found: C, 61.71; H, 3.71; N, 4.26.

step b) 4-[2-(4-chloro-phenyl)-thiazol-4-ylmethoxy]-benzaldehyde oxime

The title compound was prepared similar to the method described in example 1, step b, and was obtained as a white solid in 98.0% yield, m.p. 173°–176° C.

Analysis for: $C_{17}H_{13}ClN_2O_2S$ Calc'd: C, 59.22; H, 3.80; N, 8.12. Found.: C, 59.32; H, 3.76; N, 7.98.

step c) N-hydroxy-N-[4-[2-(4-chloro-phenyl)-thiazol-4-ylmethoxy]-phenyl-1-ylmethyl]-amine The title compound was prepared similar to the method described in example 1, step c, and was obtained as a solid in 88.1% yield, m.p. 132°–136° C. MS (CI, m/e): 347 (M+H)$^+$.

step d) 1-Hydroxy-1-[4-[2-(4-chloro-phenyl)-thiazol-4-ylmethoxy]-benzyl]-urea

The title compound was prepared similar to the method described in example 1, step d, and was obtained as a white solid in 70.5% yield, m.p. 180°–184° C. (decomposed).

Analysis for: $C_{18}H_{16}ClN_3O_3S$ Calc'd: C, 55.45; H, 4.14; N, 10.78. Found: C, 55.54; H, 4.10; N, 10.41.

EXAMPLE 15

1-Hydroxy-1-[4-[2-(4-chloro-phenyl)-thiazol-4-yl-methoxyl-benzyl]-thiourea

The title compound was prepared similar to the method described in example 1, step d, except that trimethylsilylisothiocyanate was used in place of trimethylsilylisocyanate. The product was obtained as a white solid in 71.3% yield, m.p. 163°–166° C. (decomposed).

Analysis for: $C_{18}H_{16}ClN_3O_2S$ Calc'd: C, 53.26; H, 3.97; N, 10.35. Found: C, 53.56; H, 4.00; N, 10.08.

EXAMPLE 16

1-[4-[2-(4-chloro-phenyl)-thiazol-4-ylmethoxyl-benzyl]-3-hexyl-1-hydroxy-urea

The title compound was prepared similar to the method described in example 1, step d, except that N-hexylisocyanate was used in place of trimethylsilylisocyanate. The product was obtained as a white solid in 67.5% yield, m.p. 157°–160° C. (decomposed).

Analysis for: $C_{24}H_{28}ClN_3O_3S$ Calc'd: C, 60.81; H, 5.95; N, 8.86. Found: C, 60.88; H, 6.03; N, 8.85.

EXAMPLE 17

1-Hydroxy-1-[4-[2-(4-methoxy-phenyl)-thiazol-4-yl-methoxy]-benzyl]-urea step a) 4-[2-(4-methoxy-phenyl)-thiazol-4-ylmethoxy] benzaldehyde The title compound was prepared similar to the method described in example 1, step a, and was obtained as a solid in 81.5% yield, m.p. 140°–143° C.

Analysis for: $C_{18}H_{15}NO_3S$ Calc'd: C, 66.44; H, 4.65; N, 4.30. Found: C, 66.40; H, 4.64; N, 4.25.

step b) 4-[2-(4-methoxy-phenyl)-thiazol-4-ylmethoxy] benzaldehyde oxime

The title compound was prepared similar to the method described in example 1, step b, and was obtained as a white solid in 97.7% yield, m.p. 175°–180° C.

Analysis for: $C_{18}H_{16}N_2O_3S$ Calc'd: C, 63.51; H, 4.74; N, 8.23. Found: C, 63.71; H, 4.69; N, 8.11.

step c) N-hydroxy-N-[4-[2-(4-methoxy-phenyl)-thiazol-4-ylmethoxy]-phenyl- 1-ylmethyl]-amine The title compound was prepared similar to the method described in example 1, step c, and was obtained as a solid in 84.9% yield m.p. 118°–122° C. (decomposed).

Analysis for: $C_{18}H_{18}N_2O_3S$ Calc'd: C, 63.14; H, 5.30; N, 8.18. Found: C, 63.08; H, 5.34; N, 8.07.

step d) 1-Hydroxy-1-[4-[2-(4-methoxy-phenyl)-thiazol-4-ylmethoxy]-benzyl] -urea

The title compound was prepared similar to the method described in example 1, step d, and was obtained as a white solid in 62.9% yield, m.p. 154°–156° C. (decomposed).

Analysis for: $C_{19}H_{19}N_3O_4S$ Calc'd: C, 59.21; H, 4.97; N, 10.90. Found: C, 59.23; H, 4.82; N, 10.80.

EXAMPLE 18

1-Hydroxy-1-[2-hydroxy-2-[4-(5-methyl-2-phenyl-oxazol-4-ylmethoxy)phenyl] -ethyl]-urea Step a) 5-(4-Hydroxy-phenyl)-2,2-dimethyl-2-[1,3]-dioxolane-4-one In to a cold (0° C.) solution of DL-4-hydroxymandelic acid (30.0 g, 178.6 mmol) in acetone (200 mL) was added dropwise concentrated sulfuric acid (30 mL). After stirring at 0° C. for 24 h, the mixture was poured into $H_2O$ and extracted the EtOAc. The organic extracts were dried over $MgSO_4$. Evaporation and purification by flash chromatography on silica gel (eluting solvent hexane/EtOAc 2/1) gave an off-white solid, in 71% yield, m.p. 82°–83° C.

Analysis for: $C_{11}H_{12}O_4$ Calc'd: C, 63.45; H, 5.81 Found: C, 63.00; H, 5.95

Step b) 2,2-Dimethyl-5-[4-(5-methyl-2-phenyl-oxazol-4-ylmethoxy)-phenyl] -[1,3]-dioxolan-4-one.

A mixture of 4-chloromethyl-5-methyl-2-phenyl-oxazole (10.0 g, 48.19 mmol), 5-( 4-hydroxy-phenyl)- 2,2-dimethyl-[1,3]dioxolan-4-one (10.02 g, 48.19 mmol), potassium carbonate (6.65 g, 48.19 mmol) and DMF (150 mL) was stirred at 70° C. for 5 hours. The mixture was poured into $H_2O$ and extracted with EtOAc. The organic extracts were dried over $MgSO_4$. Evaporation and purification by flash chromatography on silica gel (eluting solvent hexane/EtOAc 3/1) gave a white solid in 75% yield, m.p. 113°–115° C.

Analysis for: $C_{22}H_{21}NO_5$ Calc'd: C, 69.65; H, 5.58; N, 3.69 Found: C, 69.69; H, 5.59; N, 3.64

Step c) Hydroxy-[4-(5-methyl-2-phenyl-oxazol-4-ylmethoxy)-phenyl]-acetic acid methyl ester In to a cold (0° C.) solution of 2,2-dimethyl-5-[4-(5-methyl-2-phenyl-oxazol- 4-ylmethoxy)-1,3]dioxolan-4-one (11.5 g, 30.34 mmol) in THF (100 mL) was added dropwise sodium methoxide (25% w/w in MeOH 6.55 g, 30.34 mmol). After stirring for 30 minutes at 0° C., the mixture was allowed to come to room temperature and stirred for an additional 30 minutes. Then, the mixture was poured into $H_2O$, acidified with 2N HCl, and extracted with EtOAc. The organic extracts were dried over $MgSO_4$. Evaporation gave a white solid in 98% yield, m.p. 110°–112° C.

Analysis for: $C_{20}H_{19}NO_5$ Calc'd: C, 67.98; H, 5.42; N, 3.96 Found: C, 68.17; H, 5.42; N, 3.79

Step d) [4-(5-Methyl-2-phenyl-oxazol-4-ylmethoxy)-phenyl]-[(tetrahydro-pyran-2-yloxy)]-acetic acid methyl ester A mixture of hydroxy-[4-(5-methyl-2-phenyl-oxazol-4-ylmethoxy)-phenyl]-acetic acid methyl ester (10.79, 30.34 mmol) dihydropyran (2.76 mL, 30.34 mmol), dl-camphorsulfonic acid (100 mg) and methylene chloride (100 mL)

was stirred at room temperature for 18 hours. Then, the mixture was poured into H$_2$O, washed with aqueous NaHCO$_3$ and dried over MgSO$_4$. Evaporation gave a yellowish oil, which was carried to the next step without any further purification.

Step e) 2-[4-(5-Methyl-2-phenyl-oxazol-4-ylmethoxy)-phenyl]-2-(tetrahydro-pyran- 2-yloxy)-ethanol In to a cold (0° C.) suspension of ethyl ether (150 mL) and lithium aluminum hydride (1.139, 29.75 mmol) was added dropwise a solution of [4-(5-methyl-2-phenyl-oxazol-4-yl-methoxy)-phenyl] -[(tetrahydro-pyran-2-yloxy]-acetic acid methyl ester (13.0 g, 29.75 mmol) in THF (50 mL). After the addition the mixture was stirred for 30 minutes, quenched with EtOAc and MeOH, poured into H$_2$O, acidified with 2N HCl and extracted with EtOAc. The organic extracts were dried over MgSO$_4$. Evaporation gave a white solid, in 92% yield, m.p. 65°–67° C.

Analysis for: C$_{24}$H$_{27}$NO$_5$ Calc'd: C, 70.40; H, 6.46; N, 3.42 Found: C, 70.59; H, 6.65; N, 3.31

Step f) N-(Phenyloxycarbonyloxy)-[2-[4-[5-methyl-2-(4-trifluoromethyl-phenyl)-oxazol- 4-ylmethoxyl-phenyl]-2-(tetrahydro-pyran-2-yloxy)-ethyl]-carbamic acid phenyl ester In to a cold (–20° C.) mixture of 2-[4-(5-methyl-2-phenyl-oxazol-4-ylmethoxy)-phenyl- 2-(tetrahydro-pyran-2-yloxy)-ethanol (10.09, 24.5 mmol) triphenylphosphine (7.68 g, 29.3 mmol), N,O-bis(carbo-phenoxy)hydroxy-lamine (8.0 g, 29.3 mmol) and THF (150 mL) was added dropwise diethylazodicarboxylate (4.61 mL, 29.3 mmol). After stirring for 30 minutes at –20° C. the mixture was allowed to come to 0° C. and stirred for 2 hours. Then, the mixture was poured into H$_2$O and extracted with EtOAc. The organic extracts were dried over MgSO$_4$. Evaporation and purification by flash chromatography on silica gel (eluting solvent hexane/EtOAc 3/1) gave a white solid in 91% yield.

Analysis for: C$_{38}$H$_{36}$N$_2$O$_9$ Calc'd: C, 68.66; H, 5.46; H, 4.21 Found: C, 68.81; H, 5.46; N, 4.39

Step g) 1-Hydroxy-1-[2-[4-[5-methyl-2-(4-trifluoromethyl-phenyl)-oxazol- 4-ylmethoxy]-phenyl]-2-(tetrahydropyran-2-yloxy)-ethyl)-urea In to a high pressure vessel was placed N-(phenyloxycarbonyloxy)-[2-[4-[5-methyl-2-( 4-trifluoromethyl-phenyl)-oxazol-4-ylmethoxy]-phenyl]2-(tetrahydro-pyran-2-yloxy)-ethyl]-carbamic acid phenyl ester (10.0 g) and ammonia (20 mL) was introduced at –78° C. The vessel was tightly sealed and the mixture was allowed to stand for 24 h at room temperature. The vessel was cooled to –78° C. and the vessel opened and the ammonia was allowed to escape slowly, into a solution of HCl (2N) by raising the temperature. The residue was purified by flash chromatography on silica gel (eluting solvent EtOAc) to give a white solid, in 80% yield, m.p. 98°–100° C.

Analysis for: C$_{25}$H$_{29}$N$_3$O$_6$ Calc'd: C, 64.23; H, 6.25; N, 8.99 Found: C, 63.84; H, 6.75; N, 8.96

Step h) 1-Hydroxy-1-[2-hydroxy-2-[4-(5-methyl-2-phenyl-oxazol-4-ylmethoxy)-phenyl] -ethyl]-urea A mixture of 1-hydroxy-1-[2-[4-[5-Methyl-2-(4-trifluoromethyl-phenyl)-oxazol- 4-ylmethoxy]-phenyl] -2-(tetrahydro-pyran-2-yloxy)-ethyl)]-urea (5.0 g), MeOH (100 mL) and 4N HCl in dioxane (10 mL) was stirred at room temperature for 2 h. The mixture was poured into H$_2$O and extracted with EtOAc. The organic extracts were dried over MgSO$_4$. Evaporation and crystallization from acetone/ether/hexane gave a white solid in 95% yield, m.p. 163°–165° C.

Analysis for: C$_{20}$H$_{21}$N$_3$O$_6$ Calc'd: C, 62.65; H, 5.52; N, 10.96 Found: C, 62.52; H, 5.45; N, 10.82

EXAMPLE 19

4-Hydroxy-4-[4-[5-methyl-2-(4-trifluoromethyl-phenyl)-oxazol-4-ylmethoxyl]-benzyl] -semicarbazide Step a) 4-[5-Methyl-2-(4-trifluoromethyl-phenyl)-oxazol-4-ylmethoxy]-benzaldehyde The title compound was prepared similar to the method described in Example 6, step a, and was obtained as a white solid, m.p. 94°–95° C.

Analysis for: C$_{19}$H$_{14}$FNO$_3$ Calc'd: C, 63.16; H, 3.91; N, 3.88 Found: C, 62.93; H, 3.94; N, 3.87

Step b) 4-[5-Methyl-2-(4-trifluoromethyl-phenyl)-oxazol-4-ylmethoxy-phenyl] -methanol In to a solution of 4-[5-methyl-2-(4-trifluoromethyl-phenyl)oxazol-4-ylmethoxy]-benzaldehyde (8.5 g, 23.41 mmol) in MeOH (200 mL) was added portionwise sodium borohydride (890 mg, 23.41 mmol). After stirring for 1 hour, the mixture was poured into H$_2$O and extracted with EtOAc. The organic extracts were dried over MgSO$_4$. Evaporation gave a white solid, in 88% yield, m.p. 109°–111° C.

Analysis for: C$_{19}$H$_6$F$_3$NO$_3$ Calc'd: C, 62.81; H, 4.44; N, 3.85 Found: C, 62.84; H, 4.31; N, 3.85

Step c) 1-[4-[5-Methyl-2-(4-trifluoromethyl-phenyl)-oxazol-4-ylmethoxy]-benzyl]-1,3-bis-(tetrahydro-pyran-2-yloxy)-urea The title compound was prepared similar to the method described in example 18, step f, and was obtained as a yellow viscous oil, which was carded to the next step.

Step d) 4-Hydroxy-4-[4-[5-methyl-2-(4-trifluoromethyl-phenyl)-oxazol-4-ylmethoxy] -benzyl-semicarbazide A mixture of 1-[4-[5-methyl-2-(4-trifluoromethyl-phenyl)-oxazol-4-ylmethoxy]-benzyl]- 1,3-bis-(tetrahydro-pyran-2-yloxy)-urea (3.0 g) and hydrazine (15 mL) was stirred for 30 minutes. The mixture was poured into H$_2$O and extracted with EtOAc. The organic extracts were dried over MgSO$_4$. Evaporation and purification by flash chromatography, on silica gel (eluting solvent EtOAc/MeOH 10/1) gave a white solid in 76% yield, m.p. 143°–144° C.

Analysis for: C$_{20}$H$_{19}$F$_3$N$_4$O$_4$ Calc'd: C, 55.05; H, 4.39; N, 12.84 Found: C, 54.81; H, 4.29; N, 13.05

EXAMPLE 20

1-Isopropylidine-4-hydroxy-4-[4-[5-methyl-2-(4-trifluoromethylphenyl)-oxazol-4-ylmethoxy]-benzyl]-semicarbazone A mixture of 4-hydroxy-4-[4-[5-methyl-2-(4-trifluoromethylphenyl)-oxazol-4-ylmethoxy] -benzyl]-semicarbazide (1.0 g, 2.29 mmol) and acetone (20 mL) was stirred for 30 minutes. The volatiles were removed in vacuo and the residue was recrystallized from acetone/ether to give white solid in 63% yield, m.p. 149°–150° C.

Analysis for: C$_{23}$H$_{23}$F$_3$N$_4$O$_4$ Calc'd: C, 57.98; H, 4.87; N, 11.76 Found: C, 58.34; H, 4.80; N, 11.90

EXAMPLE 21

4-Hydroxy-4-[4-(2-phenyl-thiazol-4-ylmethoxy)-benzyl] -semicarbazide

The title compound was prepared in substantially the same manner as described in example 19, steps a–d, and was obtained as a white solid, m.p. 144°–145° C.

Analysis for: C$_{18}$H$_{18}$N$_4$O$_3$S Calc'd: C, 58.36; H, 4.90; N, 15.13 Found: C, 58.40; H, 4.28; N, 15.16

EXAMPLE 22

4-Hydroxy-4-[4-(2-phenyl-thiazol-4-ylmethoxy)-benzyl]-semicarbazide hydrochloride In to a solution of 4-hydroxy-4-[4-(2-phenyl-thiazol-4-ylmethoxy)-benzyl]-semicarbazide (1.0 g, 2.7 mmol) in THF (10 mL) was added 1N HCl in ethyl ether (1.0M, 2.7 mL, 27 mmol). After stirring for 10 minutes, additional ethyl ether (10 mL) was added and the precipitated solid was filtered and dried to give a white solid, in 88% yield, m.p. 159°–160° C.

Analysis for: $C_{18}H_{18}N_4O_3S \cdot HCl$ Calc'd: C, 53.13; H, 4.71; N, 13.77 Found: C, 53.13; H, 4.59; N, 13.80

PHARMACOLOGY

Lipoxygenase inhibiting activity and inhibition of $Cu^{+2}$ mediated peroxidation of LDL by the Formula I compounds is demonstrated in several standard pharmacological assays.

1. Inhibition of 5-Lipoxygenase in Human Whole Blood

Blood is obtained in 50–100 ml quantities from male donors. White blood cell counts and differentials are made. Two ml of blood are placed in a 15 ml polypropylene test tube. Test compounds are solubilized in dimethylsulfoxide and diluted in 1:10 in 10% bovine serum albumin in phosphate buffered saline, pH 7.4 resulting in a final dimethylsulfoxide concentration of 0.1% in the blood. Then, solutions of test compounds are added to the blood in a shaking water bath at 37° C. for 10 minutes prior to the addition of 30 µM calcium ionophore (A23187, Sigma). After ionophore administration, whole blood samples are mixed and incubated for 20 minutes at 37° C. in a shaking water bath. Incubation is terminated by placing samples in an ice bath and immediately adding ethylene glycol-bis-(β-aminoethyl ether)-N,N,N',N'-tetraacetic acid (10 mM). Samples are mixed and centrifuged at 1200×g for 15 minutes at 4° C. Preparation of samples for evaluation by RIA or ELISA is carried out by the following protocol. Plasma is removed from sample tubes, placed in 15 ml polypropylene test tubes containing 8 ml methanol, and then vonexed to precipitate protein. Samples are stored at −70° C. overnight. The next day, samples are centrifuged at 200×g for 15 minutes at 4° C. to pellet the precipitate. Samples are dried in a Savant SpeedVac Concentrator, Model SVC 200H, reconstituted to original volume with ice cold RIA or ELISA buffer, and stored at −70° C. until assayed. The assay for eicosanoids ($LTB_4$, $TxB_2$, and $PGE_2$) is performed as described by the manufacturer of the [$^3$H]-RIA kit or ELISA kit ($LTB_4$-Amersham, $TxB_2$ and $PGE_2$- Caymen Chemical).

The total eicosanoid level in 2 ml of blood is calculated and reported as ng/$10^6$ neutrophils. Significance is determined by a one-way analysis of variance with least significant difference (LSD) comparisons to control ($p \leq 0.05$) and $IC_{50}$'s (µM) are determined by regression analysis (Finney, 1978). Drug effects are expressed as percent change from control values. The results for compounds of this invention tested in this assay are presented in Table I.

TABLE I

| Compound of Example No. | Dose (µM) | % Inhibition of $LTB_4$ |
|---|---|---|
| 1 | 1 | 50 |
| 2 | 1 | 31 |

TABLE I-continued

| Compound of Example No. | Dose (µM) | % Inhibition of $LTB_4$ |
|---|---|---|
| 3 | 10 | 80 |
| 4 | 10 | 81 |
| 5 | 1 | 47 |
| 6 | 1 | 34 |
| 7 | 1 | 74 |
| 8 | 10 | 57 |
| 9 | 1 | 58 |
| 10 | 1 | 44 |
| 11 | 1 | 32 |
| 12 | 1 | 56 |
| 13 | 1 | 38 |
| 14 | 1 | 71 |
| 15 | 1 | 57 |
| 16 | 10 | 36 |
| 17 | 1 | 56 |
| 18 | 10 | 86 |
| 19 | 10 | 50 |
| 20 | 10 | 78 |
| 21 | 10 | 94 |
| 22 | 10 | 80 |

2. Ex-Vivo Measurement of Lipoxygenase Inhibition in Orally Dosed Rats

Male Sprague Dawley rats (Charles River) weighing between 180 g and 200 g were dosed orally with an invention compound (1–25 mg/kg, po) suspended in 0.5% Tween 80®. After an interval of 3 or 6 hours, the rats were anesthetized with metofane (n=4/group) and blood collected in heparinized tubes. White blood cell counts and differentials were made. One ml of blood from each animal was placed in a 5 ml plastic tube in a shaker bath at 37° C. A23187 at a final concentration of 10 µM was added to the blood and the blood vortexed and incubated for 15 min at 37° C. with gentle shaking. Incubation was terminated by vortexing sample and centrifuging immediately at 1200×G for 15 min at 4° C. The plasma was transferred to 15 ml plastic tubes each containing 8 ml of methanol to precipitate protein followed by vortexing. The samples were stored at −70° C. overnight and the next day the samples were centrifuged at 800×G for 15 min to pellet the precipitate. The samples were dried in a Savant SpeedVac Concentrator Model SVC 200H and reconstituted to the original volume with cold RIA or ELISA buffer. The reconstituted samples were stored at −70° C. until assayed. The assay for $LTB_4$ was performed according to the directions of the [$^3$H]RIA kit or ELISA kit (Seragen). The total metabolite level in 1 ml of blood is calculated and reported as ng/$10^6$ neutrophils. Significance is determined by a one-way analysis of variance with LSD comparisons to control ($p \leq 0.05$). Drug effects are expressed as percent change from control values and data for invention compounds is presented in Table II.

TABLE 11

| Compound of Example No. | Dose mg/g, p.o. | Pretreatment period. hr. | % Inhibition of $LTB_4$ |
|---|---|---|---|
| 1 | 10 | 3 | 84 |
| 1 | 10 | 6 | 75 |
| 2 | 10 | 3 | 68 |
| 2 | 10 | 6 | 72 |
| 3 | 10 | 3 | 40 |
| 5 | 10 | 3 | 66 |
| 5 | 10 | 6 | 68 |
| 6 | 5 | 6 | 70 |
| 9 | 5 | 6 | 60 |
| 10 | 5 | 6 | 67 |

TABLE 11-continued

| Compound of Example No. | Dose mg/g, p.o. | Pretreatment period. hr. | % Inhibition of LTB$_4$ |
|---|---|---|---|
| 11 | 10 | 6 | 68 |
| 17 | 10 | 6 | 69 |

3. Reverse Passive Arthus Reaction

A reverse passive Arthus reaction is induced in the pleural cavity of male Lewis rats (150–200 g; fasted overnight prior to use) by the intravenous administration of bovine serum albumin (BSA; 4 mg/0.2 ml) followed 30 minutes later by the injection of rabbit anti-BSA (1 mg/0.2 ml; lyophilized IgG fraction; Organon Teknika, West Chester, Pa.) into the right pleural space under halothane anesthesia. Drugs or vehicle (0.5% Tween-80) control are administered orally in a volume of 1 ml/100 g body weight at 1 hour prior to the anti-BSA. Animals are sacrificed at either the time of peak eicosanoid production (i.e. 5 minutes after anti-BSA for immunoreactive TxB$_2$, 10 minutes for immunoreactive LTB$_4$, 20 minutes for immunoreactive LTC$_4$) or at the time of peak neutrophil infiltration (4 hours after anti-BSA) by CO$_2$ inhalation. The pleural cavity is then exposed, the fluid exudate removed by gentle vacuum aspiration and the volume of exudate is recorded. For the determination of cellular infiltration, the pleural cavity is rinsed with 3 ml of 0.1% EDTA in sterile saline, and the recovered wash is pooled with the exudate. Cell number is determined on a model ZBI Coulter counter. For determination of eicosanoid production, undiluted pleural exudate is microfuged and the supernatant is extracted with ethanol (8–10 times volume). Extracts are either stored at −20° C., or are evaporated to dryness under a stream of N$_2$ and reconstituted in radioimmunoassay (RIA) buffer.

Eicosanoids are quantitated by RIA according to the procedure specified by the RIA kit manufacturer (Advanced Magnetics, Cambridge, Mass.). Briefly, 100 µl of $^3$H-labeled eicosanoid and 100 µl of specific antibody are sequentially added to 100 µl of extracted pleural exudate in BGG-phosphate buffer which contains 0.01M phosphate, 0.1% bovine gamma globulin and 0.1% sodium azide at pH 7.0. Antibody-bound eicosanoid is separated from unbound eicosanoid by the addition of 750 µl of dextran (0.4%)-coated charcoal (Norit A) containing 0.1% sodium azide. The mixture is centrifuged at 2000 RPM at 5° C. for 15 minutes to pellet the charcoal and adsorbed unbound eicosanoid. Antibody-bound labeled eicosanoid is quantitated by counting in a liquid scintillation counter, and is correlated to concentration by a standard curve.

The activity of standard drugs in this assay is as follows:

| Antiinflammatory Drug | Class | Dose mg/kg p.o. | % Inhibition of LTB$_4$ (ED$_{50}$) |
|---|---|---|---|
| Indomethacin | NSAID; CO inhibitor | 4 | 12 |
| Naproxen |  | 4 | 0 |
| Diclofenac |  | 10 | 0 |
| Ketoprofen |  | 10 | 35 |
| Wy-50,295-A | LO-Inhibitor | 9 | (15) |
| BW540C | Mixed CO/LO inhibitor |  | (30) |
| BW755C |  |  | (23) |
| Phenidone |  |  | (10) |

The compounds of the invention when tested in the reverse passive Arthus pleurisy assay gave the results shown in Table III.

TABLE III

| Compound of Example No. | Dose mg/kg, p.o. | % Inhibition of LTB$_4$ Synthesis |
|---|---|---|
| 1 | 25 | 69 |
| 1 | 10 | 36 |
| 3 | 25 | 26 |
| 5 | 25 | 28 |
| 6 | 10 | 45 |
| 9 | 10 | 60 |
| 10 | 10 | 99 |

4. Inhibition of Brochoconstriction in Guinea Pigs Induced by Exogenously Administered Antigen Male guinea pigs (Charles River, Wilmington, Mass.) were sensitized 3–4 weeks prior to antigen challenge by administration of 2 i.m. injections of ovalbumin, 1 into each hind limb (35 mg total). Sensitized animals (500–600 g) were fasted overnight prior to experimentation. Conscious animals were then dosed p.o. with drug or vehicle alone (0.5% Tween 80 in H$_2$O) at the indicated times prior to antigen challenge, or anesthetized animals were dosed i.v. with drug or vehicle alone (DMSO) 5 min prior to antigen challenge. Animals were anesthetized by urethane (2.8 g/kg i.p.). A carotid artery and jugular vein were cannulated to allow for the monitoring of blood pressure and the administration of drugs, respectively. The trachea was then cannulated and connected to a Harvard Apparatus rodent ventilator (S. Natick, Mass.). Spontaneous respiration was abolished by the administration of succinylcholine (2.5 mg/kg i.v.). The animals were then ventilated with room air at a rate of 65 breaths per min. Airway inflation pressure was measured using a Slatham pressure transducer (Gould Instruments, Cleveland, Ohio) connected to the tracheal cannula via a side-arm and recorded on a Grass Instruments recorder (Quincy, Mass.). The tidal volume (approximately 10 cc/kg) was adjusted to give a baseline inflation pressure of 8–10 cm H$_2$O at end inspiration. Animals were then allowed 20 min to stabilize.

Following the stabilization period, animals were given i.v. injections of pyrilamine (5 mg/kg), propranolol (0.1 mg/kg) and indomethacin (10 mg/kg) at 15, 10 and 5 min, respectively, prior to antigen challenge. This pretreatment results in an LT-dependent bronchoconstriction following antigen challenge, which was accomplished by i.v. administration of ovalbumin (10 mg/kg). Only one bronchoconstriction per animal was induced. End-inspiratory inflation pressure (in cm H$_2$O over baseline) was measured at 5 min post-antigen challenge. A mean value and standard error for the % inhibition of control bronchoconstriction in each drug-treated group was then calculated. Data for invention compounds are presented in Table IV.

TABLE IV

| Compound of Example No. | Dose mg/kg. | Administration Route | % Inhibition of bronchoconstriction |
|---|---|---|---|
| 1 | 10 | i.v. | 38 |
| 6 | 10 | i.v. | 27 |
| 6 | 25 | p.o. | 27 |
| 7 | 10 | i.v. | 24 |
| 9 | 10 | i.v. | 54 |
| 9 | 50 | p.o. | 44 |
| 10 | 10 | i.v. | 50 |
| 10 | 25 | p.o. | 24 |
| 12 | 10 | i.v. | 30 |
| 15 | 10 | i.v. | 21 |

TABLE IV-continued

| Compound of Example No. | Dose mg/kg. | Administration Route | % Inhibition of bronchoconstriction |
|---|---|---|---|
| 17 | 10 | i.v. | 50 |

5. Inhibition of Copper Ion Mediated Oxidation of Low Density Lipoprotein

In this in vitro assay, the inhibition of $Cu^{+2}$ mediated oxidation of rabbit or monkey LDL by an invention compound is determined spectrophotometricallly. Oxidation of LDL results in the formation of LDL-diene which absorbs light at 532 nm. Inhibition of oxidation of LDL leads to a decrease in absorbance at 532 nm.

Rabbit or monkey LDL is prepared according to the procedures of Havel, Eder and Gragdon, "The Distribution and Chemical Composition of Ultracentrifugally Separated Lipoproteins in Human Serum,: *J. Clin. Invest.* 34, 1345–1353 (1955) and Parhtasarathy, Wieland and Steriberg, "A Role for Endothelial Cell Lipoxygenase in the Oxidative Modification of Low Density Lipoprotein," *Proc. Natl. Acad. Sci. USA* 86, 1046–1050 (1989). Test compound solutions are prepared by dissolving the invention compounds in ethanol at concentrations up to 248 µM. The medium used is Dulbecco's phosphate buffered saline containing 0.5 mg/ml bovine serum albumin. For standards, 0 to 10 µl of an aqueous solution of 1,1,3,3-tetraethoxypropane (1 µmol/ml $H_2O$) in 4.1 ml of medium is used.

Test compound solution (100 µl) is added to 4 ml of medium in incubation tubes. To each tube is added 10 µl of LDL solution and 25 µl of aqueous copper sulfate solution (1.32 mg/ml $H_2O$). The tubes are incubated at 37° C. for 90 minutes and the oxidation reaction quenched by addition of 1 ml of thiobarbituric acid solution (0.67% in 50% acetic acid). The tubes are heated at 90° C. for 1 hour, then chilled in an ice bath and the chromophore extracted into 2 ml of n-butanol. Absorbence is read at 532 nm and the results are reported as nmols of malondialdehyde equivalents.

Significant differences ($p \leq 0.05$) are determined by the Dunnett T-test or by the Student-Newman-Keuls Test for significant differences between means. The assay is conducted using several concentrations of the inhibitor test compounds. The LDL solution concentrations at different experiments were either 1.5 mg/ml, 2.5 mg/ml or 10.3 mg/ml. The $IC_{50}$ is determined by non-linear regression, plotting log vs. % inhibition. (Reference: K. Yagi, Biochemical Medicine 15, 212–216 (1976)). The results obtained with invention compounds are shown in Table V.

TABLE V

| Example No. | $IC_{50}$ (µM) |
|---|---|
| 1 | 1.1 |
| 2 | 0.56 |
| 4 | 0.81 |
| 14 | 1.1 |

Pharmaceutical Composition

When the compounds of the invention are employed in the treatment of allergic airway disorders, inflammation, or atherosclerosis, they can be formulated into oral dosage forms such as tablets, capsules and the like. The compound can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be administered parentemily, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired the dosage may be divided into convenient subunits administered at suitable times throughout the day.

What is claimed is:

1. A compound according to the formula:

wherein:

$R^1$ and $R^3$ are independently hydrogen, halogen, $C_1$-$C_6$ alkyl, $C_1$-$C_6$ alkoxy, trifluoromethyl, or $C_1$-$C_6$ trifluoroalkoxy;

$R_2$ is hydrogen or methyl;

$R^4$ is hydrogen, methyl or hydroxy;

$R^5$ is hydrogen, —$NH_2$, $C_1$-$C_6$ alkyl, $C_6$-$C_{10}$ aryl, $C_6$-$C_{10}$ aryl-$C_1$-$C_6$ alkylene, or —N=C(CH$_3$)$_2$;

X and Y are independently O or S;

and n is 0 or 1; or a pharmaceutically acceptable salt thereof.

2. A compound according to claim 1 which is selected from:

1-hydroxy-1-[4-(5-methyl-2-phenyl-oxazol-4-yl-methoxy)-benzyl]-urea,

1-[3-chloro-4-[5-methyl-2-phenyl-oxazol-4-ylmethoxy-)benzyl]-1-hydroxy-urea,

1-[2-chloro-4-(5-methyl-2-phenyl-oxazol-4-ylmethoxy)-benzyl]-1-hydroxy-urea, 1-hydroxy-1-[3-methoxy-4-(5-methyl-2-phenyl-oxazol-4-ylmethoxy)-benzyl]-urea, 1-[3-fluoro-4-(5-methyl-2-phenyl-oxazol-4-ylmethoxy)-benzyl]-1-hydroxy-urea, 1-hydroxy-1-[4-[5-methyl-2-(4-trifluoromethyl-phenyl)-oxazol-4-ylmethoxy]-benzyl]-urea, 1-hydroxy-1-[4-[5-methyl-2-(4-trifluoroethoxy-phenyl)- oxazol-4-ylmethoxy]-benzyl]-urea, 1-hydroxy-1-[1-[4-(5-methyl-2-phenyl-oxazol-4-yl-methoxy)-phenyl]-ethyl]-urea, 1-hydroxy-1-[4-(2-phenyl-oxazol-4-ylmethoxy)-benzyl]-urea, 1-hydroxy-1-[(4-(2-phenyl-thiazol-4-ylmethoxy)-benzyl]-urea, 1-hydroxy-1-[4-[2-(4-trifluoromethyl-phenyl)-oxazol-4-ylmethoxy]-benzyl]-urea 1-hydroxy-1-[4-[2-(4-trifluoromethyl-phenyl)-thiazol-4-ylmethoxy]-benzyl]-urea, 3-(4-fluorophenyl)-1-hydroxy-1-[4-[2-(4-trifluoromethyl-phenyl)-thiazol-4-ylmethoxy]-benzyl]-urea, 1-[4-[2-(4-chlorophenyl)-thiazol-4-ylmethoxy)-benzyl]-3-hexyl-1-hydroxy-urea, 1-hydroxy-1-[4-[2-(4-methoxyphenyl)-thiazol-4-yl-methoxy]-benzyl]-urea, 1-[4-[2-(4-chlorophenyl)-thiazol-4-ylmethoxy]-benzyl]-1-hydroxy-thiourea, 1-[4-[2-(4-chlorophenyl)-thiazol-4-ylmethoxy]-benzyl]-3-hexyl-1-hydroxy-urea, 1-hydroxy-1-[2-hydroxy-2-[4-(5-methyl-2-phenyl-oxazol-4-ylmethoxy)-phenyl]-ethyl]urea, 1-hydroxy-4-[4-[5-methyl-2-(4-trifluoromethyl-phenyl)-oxazol-4-ylmethoxy]-benzyl]semicarbazide, 1-isopropylidine-4-hydroxy-4-[4-[5-methyl-2-(4-trifluoromethyl-phenyl)-oxazol- 4-ylmethoxy]-benzyl]-semicarbazone, 4-hydroxy-4-[4-(2-phenyl-thiazol-4-ylmethoxy)-benzyl]-semicarbazide, and 4-hydroxy-4-[4-(2-phenyl-thiazol-4-ylmethoxy)-benzyl]-semicarbazide hydrochloride.

3. A method of treating inflammation in a mammal which comprises administration thereto a therapeutically effective amount of a compound having the formula:

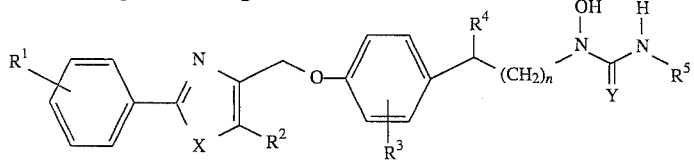

wherein:

$R^1$ and $R^3$ are independently hydrogen, halogen, $C_1$-$C_6$ alkyl, $C_1$-$C_6$ alkoxy, trifluoromethyl, or $C_1$-$C_6$ trifluoroalkoxy;

$R_2$ is hydrogen or methyl;

$R^4$ is hydrogen, methyl or hydroxy;

$R^5$ is hydrogen, —$NH_2$, $C_1$-$C_6$ alkyl, $C_6$-$C_{10}$ aryl, $C_6$-$C_{10}$ aryl-$C_1$-$C_6$ alkylene, or —$N$=$C(CH_3)_2$;

X and Y are independently O or S;

and n is 0 or 1; or a pharmaceutically acceptable salt thereof.

4. A method of treating bronchoconstriction in a mammal which comprises administration thereto a therapeutically effective amount of a compound having the formula:

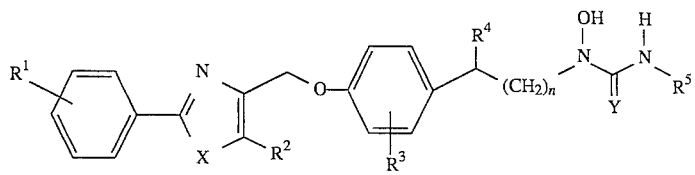

wherein:

$R^1$ and $R^3$ are independently hydrogen, halogen, $C_1$-$C_6$ alkyl, $C_1$-$C_6$ alkoxy, trifluoromethyl, or $C_1$-$C_6$ tfifluoroalkoxy;

$R_2$ is hydrogen or methyl;

$R^4$ is hydrogen, methyl or hydroxy;

$R^5$ is hydrogen, —$NH_2$, $C_1$-$C_6$ alkyl, $C_6$-$C_{10}$ aryl, $C_6$-$C_{10}$ aryl-$C_1$-$C_6$alkylene, or —$N$=$C(CH_3)_2$;

X and Y are independently O or S;

and n is 0 or 1; or a pharmaceutically acceptable salt thereof.

5. A method of inhibiting atherosclerotic plaque formation in a mammal which comprises administration thereto a therapeutically effective amount of a compound having the formula:

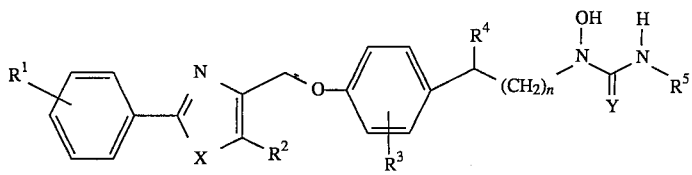

wherein:
- $R^1$ and $R^3$ are independently hydrogen, halogen, $C_1$-$C_6$ alkyl, $C_1$-$C_6$ alkoxy, trifluoromethyl, or $C_1$-$C_6$ trifluoroalkoxy;
- $R_2$ is hydrogen or methyl;
- $R^4$ is hydrogen, methyl or hydroxy;
- $R^5$ is hydrogen, —$NH_2$, $C_1$-$C_6$ alkyl, $C_6$-$C_{10}$ aryl, $C_6$-$C_{10}$ aryl-$C_1$-$C_6$ alkylene, or —$N=C(CH_3)_2$;
- X and Y are independently O or S;

and n is 0 or 1; or a pharmaceutically acceptable salt thereof.

6. A pharmaceutical composition for the treatment of inflammation or bronchoconstriction or inhibition of atherosclerotic plaque formation which comprises a pharmaceutical carrier and a therapeutically effective amount of a compound having the formula:

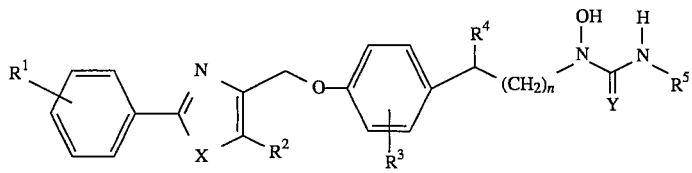

wherein:
- $R^1$ and $R^3$ are independently hydrogen, halogen, $C_1$-$C_6$ alkyl, $C_1$-$C_6$ alkoxy, trifluoromethyl, or $C_1$-$C_6$ trifluoroalkoxy;
- $R_2$ is hydrogen or methyl;
- $R^4$ is hydrogen, methyl or hydroxy;
- $R^5$ is hydrogen, —$NH_2$, $C_1$-$C_6$ alkyl, $C_6$-$C_{10}$ aryl, $C_6$-$C_{10}$ aryl-$C_1$-$C_6$ alkylene, or —$N=C(CH_3)_2$;
- X and Y are independently O or S;

and n is 0 or 1; or a pharmaceutically acceptable salt thereof.

\* \* \* \* \*